(12) United States Patent  (10) Patent No.: US 8,314,781 B2
Pittenger et al.  (45) Date of Patent: Nov. 20, 2012

(54) HOSPITAL BED HAVING MULTIPLE TOUCHSCREEN DISPLAYS

(75) Inventors: William G. Pittenger, Aurora, IN (US); James M. Allen, Batesville, IN (US); Keith A. Huster, Sunman, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 304 days.

(21) Appl. No.: 12/714,013

(22) Filed: Feb. 26, 2010

(65) Prior Publication Data

US 2011/0210925 A1  Sep. 1, 2011

(51) Int. Cl.
G06F 3/045 (2006.01)

(52) U.S. Cl. ...................................... 345/174; 178/18.06

(58) Field of Classification Search .......... 345/156–179; 705/2; 5/611, 616; 178/18.01–18.07; 601/49
See application file for complete search history.

(56) References Cited

U.S. PATENT DOCUMENTS

| | | | |
|---|---|---|---|
| 5,715,548 A | 2/1998 | Weismiller et al. | |
| 5,771,511 A | 6/1998 | Kummer et al. | |
| 7,017,208 B2 | 3/2006 | Weismiller et al. | |
| 7,237,287 B2 | 7/2007 | Weismiller et al. | |
| 7,296,312 B2 | 11/2007 | Menkedick et al. | |
| 7,472,439 B2 | 1/2009 | Lemire et al. | |
| 7,510,186 B2 * | 3/2009 | Fleckenstein | 273/149 R |
| 7,758,411 B2 * | 7/2010 | Crawford et al. | 463/13 |
| 8,052,519 B2 * | 11/2011 | Soltys | 463/25 |
| 2006/0044214 A1 * | 3/2006 | Hong | 345/1.1 |
| 2006/0058091 A1 * | 3/2006 | Crawford et al. | 463/13 |
| 2006/0101581 A1 | 5/2006 | Blanchard et al. | |
| 2007/0157385 A1 | 7/2007 | Lemire et al. | |
| 2007/0163043 A1 | 7/2007 | Lemire et al. | |
| 2007/0163045 A1 | 7/2007 | Becker et al. | |
| 2007/0169268 A1 | 7/2007 | Lemire et al. | |
| 2007/0174964 A1 | 8/2007 | Lemire et al. | |
| 2007/0174965 A1 | 8/2007 | Lemire et al. | |
| 2007/0213116 A1 * | 9/2007 | Crawford et al. | 463/16 |
| 2008/0172789 A1 * | 7/2008 | Elliot et al. | 5/616 |
| 2008/0235872 A1 | 10/2008 | Newkirk et al. | |
| 2011/0144548 A1 * | 6/2011 | Elliott et al. | 601/49 |

OTHER PUBLICATIONS

"FIN24C uSerDes™ Low-Voltage 24-Bit Bi-Directional Serializer/Deserializer", Fairchild Semiconductor Corporation, Oct. 2006.
"i.MX35 Multimedia Applications Processors Consumer and industrial portfolio", Freescale Semiconductor, Inc, 2009.
"1.2V to 3.6V, 12-Bit, Nanopower, 4-Wire Micro Touch Screen Controller with I2 C™ Interface", Texas Instruments Corporation, 2009.

* cited by examiner

*Primary Examiner* — Vijay Shankar
(74) *Attorney, Agent, or Firm* — Barnes & Thornburg LLP (57) ABSTRACT

Embodiments of an apparatus for controlling a plurality of modules coupled to a communications network of a bed are disclosed. The apparatus may comprise an interface module, a plurality of user interfaces, and a plurality of dedicated data links. The interface module may include a transceiver coupled to the communications network, a processor configured to output graphics data, and a plurality of transmitters configured to receive the graphics data and generate a plurality of synchronous graphics signals. Each of the plurality of user interfaces may include a graphical display. Each of the plurality of dedicated data links may be coupled to one of the plurality of transmitters and to one of the plurality of user interfaces.

21 Claims, 4 Drawing Sheets

HOSPITAL BED HAVING MULTIPLE TOUCHSCREEN DISPLAYS

BACKGROUND

The present disclosure generally relates to person-support apparatuses, such as hospital beds that may be used in healthcare environments (e.g., hospitals, nursing homes, etcetera). In particular, the present disclosure relates to systems and methods of controlling a person-support apparatus using multiple touchscreen displays.

Person-support apparatuses may comprise beds, chairs, stretchers, seats, mattresses, therapy surfaces, operating room tables, furniture, and the like, or other apparatuses that support a person. Hospital beds and stretchers, hospital mattresses, and wheelchairs are examples of such apparatuses that facilitate patient care and transport in healthcare environments. Consumer beds, chairs, and furniture are also examples of person-support apparatuses, as are seats for vehicles, businesses, and venues.

Person-support apparatuses intended for use in healthcare environments are known to include various operational functions or features including support surface movement and reconfiguration, environmental control (e.g., lighting and television control), and nurse call system interfacing. Some person-support apparatuses are also configured to provide therapeutic functions or features to a patient on the support surface, including, for example, pressure redistribution, turning assistance, rotation, percussion and vibration, low air loss, and the like.

Person-support apparatuses that provide one or more of such operational and therapeutic functions or features typically include one or more user interfaces for a caregiver and/or the patient to control the operation of the functions or features. These user interfaces are often provided in user modules which are either fixed in or coupled to a barrier element of the person-support apparatus or are provided as pendants or removable modules that may be stored in the barrier elements. A conventional user module typically includes an independent computing engine for controlling the associated user interface and circuitry for communicating directly with a controller, a control system, or a communications network of the apparatus. In a person-support apparatus containing two or more such user modules, a synchronization algorithm must be employed to coordinate the operation of the user modules.

SUMMARY

The present invention comprises one or more of the features recited in the appended claims and/or the following features which, alone or in any combination, may comprise patentable subject matter:

According to one aspect, an apparatus for controlling a plurality of modules coupled to a communications network of a bed may comprise an interface module, a plurality of user interfaces, and a plurality of dedicated data links. The interface module may include a transceiver coupled to the communications network, a processor configured to output graphics data, and a plurality of transmitters configured to receive the graphics data and generate a plurality of synchronous graphics signals. Each of the plurality of user interfaces may include a graphical display. Each of the plurality of dedicated data links may be coupled to one of the plurality of transmitters and to one of the plurality of user interfaces.

Each of the plurality of user interfaces may lack a transceiver coupled to the communications network. Each of the plurality of transmitters may include a serializer configured to receive the graphics data from the processor via a parallel signal path, convert the graphics data into a serial graphics signal, and transmit the serial graphics signal via the dedicated data link coupled to the transmitter. Each of the plurality of user interfaces may further include a deserializer configured to receive the serial graphics signal via the dedicated data link coupled to the user interface, reconvert the serial graphics signal into graphics data, and provide the graphics data to the graphical display of the user interface via a parallel signal path.

Each of the plurality of dedicated data links may include a twisted pair serial cable. Each of the plurality of graphical displays may be configured to output the graphics data to provide a multi-level, menu-driven user interface for the bed. The graphics data may include at least one of a bed status, a menu of selectable bed therapies, a description of a selected therapy, a menu of control options for the selected therapy, and a record of patient information.

Each of the plurality of user interfaces may further include an input device configured to generate a command signal in response to a user interaction and transmit the command signal to the interface module via the dedicated data link coupled to the user interface. The input device of each user interface may include a touchscreen positioned in proximity to the graphical display of the user interface and a controller coupled to the touchscreen. The controller may be configured to generate the command signal in response to a user interaction with the touchscreen. The processor may be configured to evaluate the command signal and instruct the transceiver to generate a network message on the communications network in response to the command signal. At least one of the plurality of user interfaces may be remote from the interface module.

According to another aspect, a person-support apparatus may comprise a communications network coupling a plurality of modules, an interface module coupled to the communications network, a first user interface, and a second user interface. Each of the plurality of modules may be configured to control a function of the person-support apparatus. The first user interface may include a first input device and a first graphical display. The second user interface may include a second input device and a second graphical display. The interface module may be configured to transmit a first synchronous graphics signal to the first user interface via a first dedicated serial link and transmit a second synchronous graphics signal to the second user interface via a second dedicated serial link.

The interface module may include a first serializer configured to convert a graphic into the first synchronous graphics signal and a second serializer configured to convert the graphic into the second synchronous graphics signal. The first user interface may further include a first deserializer configured to reconvert the first synchronous graphics signal into the graphic. The second user interface may further include a second deserializer configured to reconvert the second synchronous graphics signal into the graphic. The graphic may be displayed on both the first and second graphical displays.

The interface module may be configured to receive a command signal from either the first input device via the first dedicated serial link or the second input device via the second dedicated serial link and generate a network message on the communications network in response to the command signal. The person-support apparatus may further comprise an articulated support surface. One of the plurality of modules may be operable to reposition the articulated support surface in response to the network message. The first user interface may be remote from the interface module. The second user interface may be both remote from the interface module and remote from the first user interface.

According to yet another aspect, an interface module may comprise a processor, a memory, a plurality of serial interfaces, and a transceiver configured to communicate with a plurality of bed control modules over a communications network. Each serial interface may be configured to communicate with a touchscreen display over a dedicated serial link. The memory may include a plurality of instructions which, when executed by the processor, cause the processor to retrieve graphics data from the memory and output the graphics data to the plurality of serial interfaces to be synchronously transmitted to the touchscreen displays.

The memory may further include instructions which, when executed by the processor, cause the processor to receive a first command signal via one of the plurality of serial interfaces, determine a network message in response to the first command signal, and instruct the transceiver to transmit the network message. The memory may further include instructions which, when executed by the processor, cause the processor to receive a second command signal via another of the plurality of serial interfaces and determine a priority of execution for the first and second command signals. The first command signal may indicate a therapy selected by a user. The network message may cause one or more of the plurality of bed control modules to deliver the selected therapy.

The memory may further include instructions which, when executed by the processor, cause the processor to retrieve updated graphics data from the memory in response to the first command signal and output the updated graphics data to the plurality of serial interfaces to be synchronously transmitted to the touchscreen displays. The updated graphics data may include at least one of a bed status, a description of the selected therapy, and a menu of control options for the selected therapy.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but, on the contrary, the intention is to cover all modifications, equivalents, and alternatives falling within the spirit and scope of the invention as defined by the appended claims.

In the following description, numerous specific details such as types and interrelationships of hardware components, software opcodes, logic implementations, and logic partitioning/integration choices may be set forth in order to provide a more thorough understanding of the present disclosure. It will be appreciated, however, by one skilled in the art that embodiments of the disclosure may be practiced without such specific details. In other instances, control structures, gate level circuits, and full software instruction sequences have not been shown in detail in order not to obscure the invention. Those of ordinary skill in the art, with the included descriptions, will be able to implement appropriate functionality without undue experimentation.

Embodiments of the disclosed systems and methods may be implemented in hardware, firmware, software, or any combination thereof. Embodiments of the disclosed systems and methods implemented in a person-support apparatus may include one or more point-to-point interconnects between components and/or one or more bus-based interconnects between components. Generally, these interconnects, or signal paths, may be embodied as any number of links, wires, cables, light guides, printed circuit board traces, buses, intervening devices, and/or the like. Embodiments of the disclosed systems and methods may also be implemented, in part, as instructions stored on a tangible, machine-readable medium (i.e., a memory), which may be read and executed by one or more processors. A tangible, machine-readable medium may include any mechanism for storing or transmitting information in a form readable by a machine (e.g., a processor). For example, a tangible, machine-readable medium may include read only memory (ROM), random access memory (RAM), magnetic disk storage, optical storage, flash memory, and/or other types of memory devices.

Figure 1:
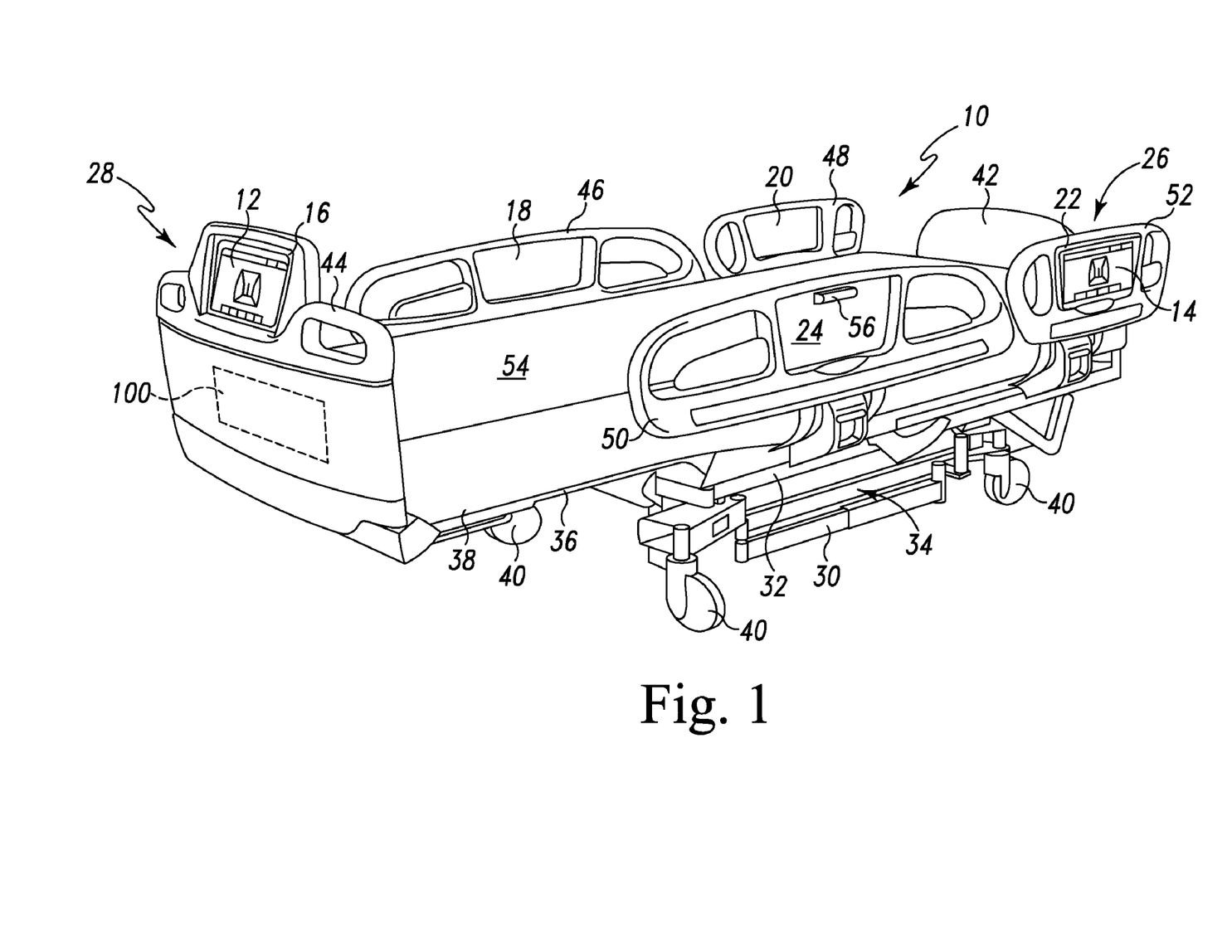
FIG. 1 is a perspective view showing an embodiment of a person-support apparatus including multiple user interfaces.

Referring now to FIG. 1, there is shown an exemplary person-support apparatus, illustratively embodied as a bed 10 including multiple user interfaces 12, 14 and multiple user interface mounting regions 16, 18, 20, 22, 24. Bed 10 generally includes a head end 26 and a foot end 28, a base 30, a frame 32 supported above the base 30 by a lift mechanism 34, a mattress support deck 36, a mattress 38, wheels or casters 40, and a number of barrier elements 42, 44, 46, 48, 50, 52. Although the present disclosure generally refers to the bed 10, it will be appreciated that the concepts illustrated and described herein are applicable to other person support apparatuses, including, for example, but not limited to, stretchers, wheelchairs, seats, chairs, or other apparatuses capable of supporting a person.

The mattress 38 defines a person-support surface 54 which is bounded by the barrier elements 42-52. In particular, the person-support surface 54 is generally surrounded by a headboard 42 mounted to the mattress support deck 36 at the head end 26 of the bed 10, a footboard 44 mounted to the mattress support deck 36 at a foot end 28 of the bed 10, a pair of siderails 46 and 48 mounted to the mattress support deck 36 adjacent to one side of the mattress 38, and another pair of siderails 50 and 52 mounted to the mattress support deck 36 adjacent to an opposite side of the mattress 38. Some, or all, of the barrier elements 42-52 (e.g., siderails 46-52) may be movable relative to the person-support surface 54, such that a patient's egress is impeded when the barrier elements 42-52 are in an "up" position, but the patient's egress is allowed when one or more of the barrier elements 42-52 are in a "down" position.

The bed 10 is configured to adjustably position the mattress support deck 36 (and, hence, the mattress 38 and the person-support surface 54) relative to the base 30. For instance, the lift mechanism 34 of bed 10 is operable to raise and lower the height of the frame 32 and the mattress support deck 36 above the base 30. In some embodiments, the mattress support deck 36 may be articulated, allowing further repositioning of the person-support surface 54. In such embodiments, separate sections of the articulated mattress support deck 36 may be repositioned relative to the frame 32 and relative to each other. The mattress support deck 36 may, for example, be adjustably positioned in a general incline from the head end 26 to the foot end 28, or vice versa. Additionally, the mattress deck 36 may be adjustably positioned such that an upper torso area of the mattress 38 is positioned between minimum and maximum incline angles (e.g., 0-54 degrees) relative to horizontal or bed flat, and the mattress support deck 36 may also be adjustably positioned such that a thigh area of the mattress 38 is positioned between minimum and maximum bend angles (e.g., 0-35 degrees) relative to horizontal or bed flat. The mattress support deck 36 or portions thereof may be adjustably positioned in other orientations, and such other orientations are contemplated by this disclosure.

Various structures and devices may be provided to adjustably position the mattress support deck 36. Such structures and devices may include, for example, linkages, drives, and other mechanical or electrometrical movement members coupled between the base 30 and the frame 32 and/or between the frame 32 and mattress support deck 36. In some embodiments, the mattress 38 may include a number of air bladders that may be used to provide positioning and/or therapy, for example, pressure redistribution therapy, rotational therapy, percussion therapy, vibration therapy, low air loss therapy, and positioning to assist turning of a patient. In such embodiments, the bed 10 may include structures and devices (e.g., a pneumatic control system) to selectively inflate and deflate the air bladders of the mattress 38. It will be appreciated that the bed 10 may include other known electrical and electromechanical devices that provide additional functions and features. For instance, in some embodiments, a number of sensors may be provided to enable automatic detection of a change in the status of the bed 10. By way of illustrative example, the bed 10 may include one or more sensors which detect a change in the position of the support surface 54 or a portion thereof and/or one or more siderail sensors which detect whether each siderail 46-52 is being raised or lowered or is in an "up" or "down" position.

Each of the structures and devices which control the operational and therapeutic functions or features of the bed 10 may be coupled to an electrical control system that provides control, monitoring, and interfacing of the various systems of bed 10. The electrical control system of the bed 10 may be illustratively embodied as a communications network 96 coupling a number of bed control modules 98 (shown in FIG. 3). For instance, in some embodiments, the bed 10 may include a number of modules connected via an Echelon®-based network, as described in U.S. Pat. Nos. 5,715,548 and 5,771,511, the disclosures of which are hereby expressly incorporated by reference in their entirety. In other embodiments, the bed 10 may include a number of modules connected via a controller area network, as described in U.S. Pat. No. 7,296,312, the disclosure of which is hereby expressly incorporated by reference in its entirety. It will be appreciated by those of skill in the art that other types of network configurations are possible (e.g., wireless) and that the bed 10 may include multiple networks.

In general, each bed control module 98 is configured to operate or control one of the operational or therapeutic functions or features of the bed 10 described above (although a module may also control more than one function or feature). The term "module" generally describes a system of hardware, firmware, and/or software relating to a function or feature of the bed 10. For instance, a bed control module 98 may include a processor (e.g., one or more microprocessors or microcontrollers) and a memory (e.g., a volatile or non-volatile computer memory) storing commands, data, and/or instructions. These and other hardware elements (e.g., circuitry for communicating over the network 96) may be mounted on a circuit board or substrate, which may be coupled to or embedded in a physical component of the bed 10, such as the base 30, the frame 32, the mattress support deck 36, the mattress 38, any of the barrier elements 42-52, or the like. The electrical control system may be configurable to add or remove bed control modules 98 to or from the network 96 as required according to a particular use of the bed 10, usage setting (i.e., hospital, clinical, or home environment, etcetera), patient type (i.e., immobile, bariatric, ICU, maternity, etcetera), or other parameters.

The bed 10 is also provided with a number of user interfaces 12, 14 to enable a person (e.g., a caregiver or a patient) to electronically control the operational or therapeutic functions or features of the bed 10. Although illustrated as having two user interfaces in the figures, it is contemplated that the bed 10 may include any number of user interfaces. As will be described in greater detail below (with reference to FIG. 3), each user interface 12, 14 is operably coupled via a dedicated data link 102, 104 to an interface module 100 of the bed 10. The interface module 100 is operably coupled to the bed control modules 98 of the electrical control system via the network 96. The interface module 100 may be mounted in, embedded in, or coupled to any suitable physical component of the bed 10 (e.g., within the footboard 44, as shown in FIG. 1). The incorporation of multiple user interfaces 12, 14 may allow a person to operate the bed 10 from several different locations around the perimeter, using any one of the multiple user interfaces 12, 14. Two or more persons may also work together using the multiple user interfaces 12, 14 to complete an operation, such as weighing a patient.

Several user interface mounting regions 16-24 are provided in the barrier elements 42-52 of the bed 10, as shown in FIG. 1. In some embodiments, a user interface mounting bracket 56 may be provided to fixedly, pivotably, or releasably secure one of the user interfaces 12, 14 within or to a mounting region 16-24. In the illustrative embodiment of FIG. 1, the user interface 12 is secured to the mounting region 16 of the footboard 44, and the user interface 14 is secured to the mounting region 22 of the siderail 52. In addition to the mounting regions 16-14, one or more user interfaces may be coupled to other physical components of the bed 10 (e.g., the headboard 42), by a mounting bracket, beam, support, or gooseneck, or may be positionable adjacent or alongside of the bed 10, such as on a service cart, support column, overbed table, adjacent wall, or the like. In some embodiments, each user interface 12, 14 may be remote from the interface module 100 and/or remote from the other user interfaces. According to the present disclosure, the term "remote" refers to elements which are positioned in or on different physical components of the bed 10, such as different barrier elements 42-52. Thus, in the embodiment of FIG. 1, the various user interface mounting regions 16-24 are remote from one another, and the user interface 14 is remote from both the interface module 100 and the user interface 12.

Figure 2:
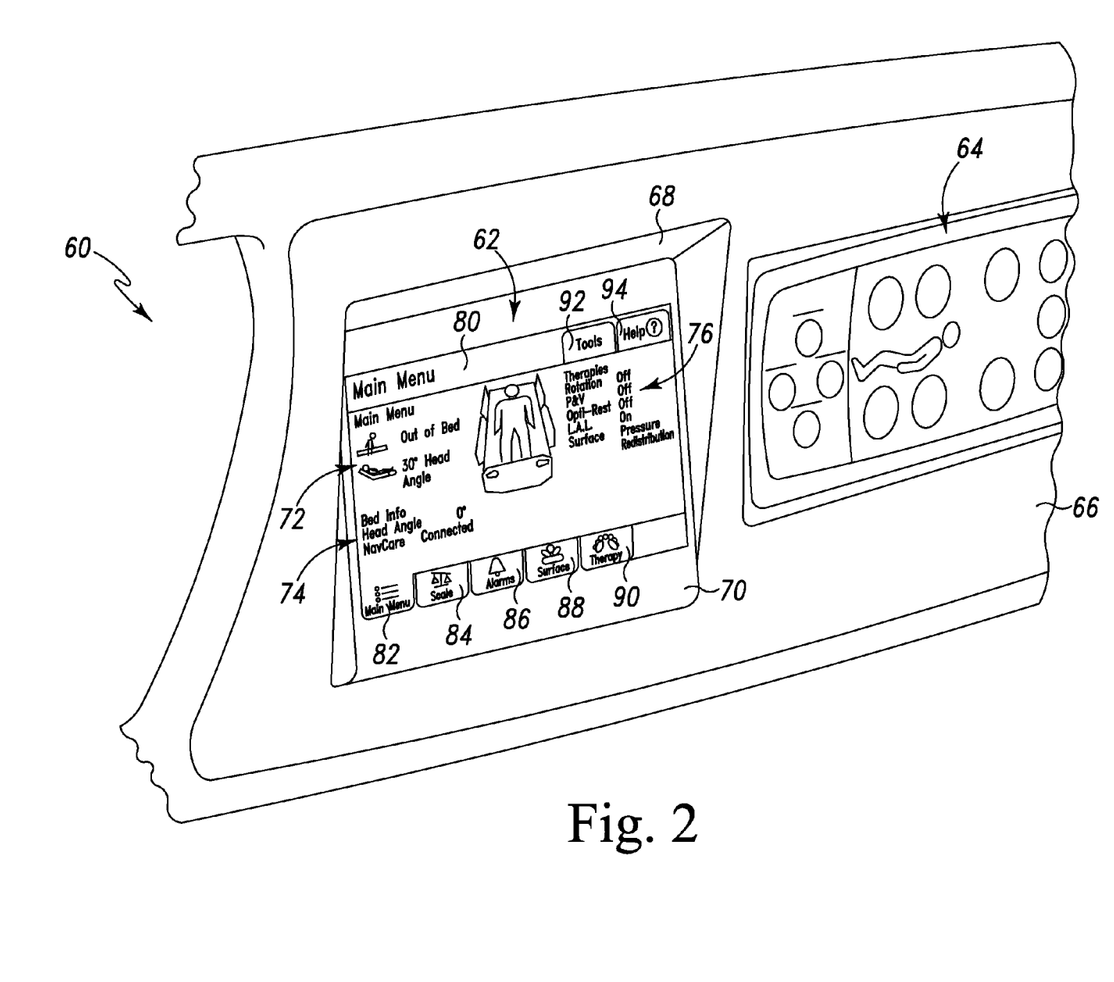
FIG. 2 is perspective view showing an embodiment of a user interface which may be mounted in a barrier element of the person-support apparatus of FIG. 1, the user interface including a touchscreen display and a number of hardpanel controls.

Referring now to FIG. 2, details are shown of one illustrative user interface 60 which could be mounted in one of the barrier elements 42-52 of the bed 10 of FIG. 1. The user interface 60 generally includes a touchscreen display 62 and hardpanel controls 64, both mounted in a panel 66 of a barrier element. As shown in FIG. 2, the touchscreen display 62 is mounted at an angle, creating a recess 68 from the panel 66, and the hardpanel controls 64 are positioned on the panel 66 adjacent to the touchscreen display 62. The touchscreen display 62 is encased in a housing 70, which may be constructed of molded plastic or another suitable material. The housing 70 may be molded into the panel 66 of the barrier element such that it is an integral part thereof. In other embodiments, such as described above with reference to FIG. 1, the housing 70 may be pivotably coupled to the barrier element. It will be appreciated that the user interface 60 may, alternatively or additionally, include input devices other than those shown in FIG. 2, including, but not limited to, a microphone, a voice or sound recognition device, a keyboard, a touch pad, a track ball, or the like.

In general, the hardpanel controls 64 are electromechanical switches such as membrane buttons or keys that may be depressed, turned, or otherwise physically displaced to some degree to activate or deactivate a function or feature of the bed 10. The hardpanel controls 64 may be programmed to control movement functions of the bed 10, such as adjustably positioning the mattress support deck 36. In this manner, the hardpanel controls 64 may serve as an input device of the user interface 60. Each hardpanel control 64, in conjunction with associated circuitry, will generate a command signal when physically displaced that will be communicated to the interface module 100. In addition, the hardpanel controls 64 may be programmed to control any other function or feature of the bed 10, including browsing and selecting menu options displayed on the touchscreen display 62. In some embodiments, such as where the touchscreen display 62 also serves as an input device, for example, the user interface 60 need not include hardpanel controls 64.

The touchscreen display 62 is configured to function both as an input device and an output device (i.e., a display) for the user interface 60. The touchscreen display 62 includes a liquid-crystal display (LCD) or similar display for visually outputting text and graphics to a user. In the illustrated embodiment, the touchscreen display 62 includes a high pixel-density (e.g., greater than 640×480 pixel resolution) and high contrast screen, as well as backlighting to improve visibility from various angles. The touchscreen display 62 also includes a sensor in the form of a transparent touchscreen layered above the LCD, providing a touch sensitive surface so that particular display elements may be selected or otherwise manipulated by touching the display surface with a finger or other object and/or dragging the finger or other object across the surface. The touchscreen may employ electrical resistance, surface capacitance, projected capacitance, mechanical energy, surface acoustic waves, infrared light, optical imaging, or any other known technology to determine when and where a user touches the touchscreen display 62. In response to a user interaction, the touchscreen, in conjunction with associated circuitry, will generate a command signal to be communicated to the interface module 100. In some embodiments, such as where the user interface 60 includes hardpanel controls 64 as an input device, for example, the user interface 60 may include a passive display, rather than the touchscreen display 62.

The touchscreen display 62 shown in FIG. 2 is configured to provide a multi-level, menu-driven user interface for the bed 10. The touchscreen display 62 generally includes a "dynamic" interface, meaning that the touchscreen display 62, including graphics 72, 74, 76, 78, 80 and controls 82, 84, 86, 88, 90, 92, 94, can change substantially in real time, as bed functions and features are activated, in progress, or deactivated, or as a patient's position or physiological status changes, for example. Touchscreen controls 82-90 each correspond to a main function or feature of the bed 10 and are in the form of tabs positioned along a lower portion of the screen. The user can quickly switch between menu pages by activating (e.g., by contact) the tab associated with the next desired function or feature. Each menu page may include informational display elements as well as display elements that may be selected or otherwise manipulated by touch in order to set or monitor aspects of the various functions of features associated with the menu pages. Each control 82-90 includes both a brief text description and a graphical icon illustrative of the function that may be selected by touching the control 82-90. Touchscreen controls 92, 94 are generally used less frequently than controls 82-90 and are, therefore, positioned in another part of the screen.

In the illustrative embodiment shown in FIG. 2 (showing the "Main Menu" tab, selectable by control 82), the touchscreen display 62 also includes a first dynamic region 72, a second dynamic region 74, a third dynamic region 76, a fourth dynamic region 78, and a fifth dynamic region 80. The first dynamic region 72 is an informational status area indicating the current status of alarms that have been set or enabled for bed 10. For instance, if the "out of bed" alarm and the "30 degree head angle" alarm are both activated, as shown, graphical icons and textual messages indicative of these alarms are displayed in region 78. The second dynamic region 74 is an informational status area indicating the current status of the bed 10. In the illustration, the region 74 displays the current value of the head of bed angle in degrees and the status of the bed's connection to an external system or network (such as the Hill-Rom® NaviCare™ system). The third dynamic region 76 is an informational status area indicating the current status of the person-support surface 54 and available therapies, such as "Rotation," percussion and vibration ("P&V"), "Opti-Rest," airflow or "low air loss" ("L.A.L."), and "Surface" (pressure redistribution). The fourth dynamic region 78 includes a graphical representation of a patient positioned on the bed 10; portions of this graphical representation may become animated in response to the activation or deactivation of certain functions or features. The fifth dynamic region 80 displays the title of the currently active menu screen in textual form. It will be appreciated that this graphical arrangement is exemplary and that alternative display and control arrangements may be utilized.

Figure 3:
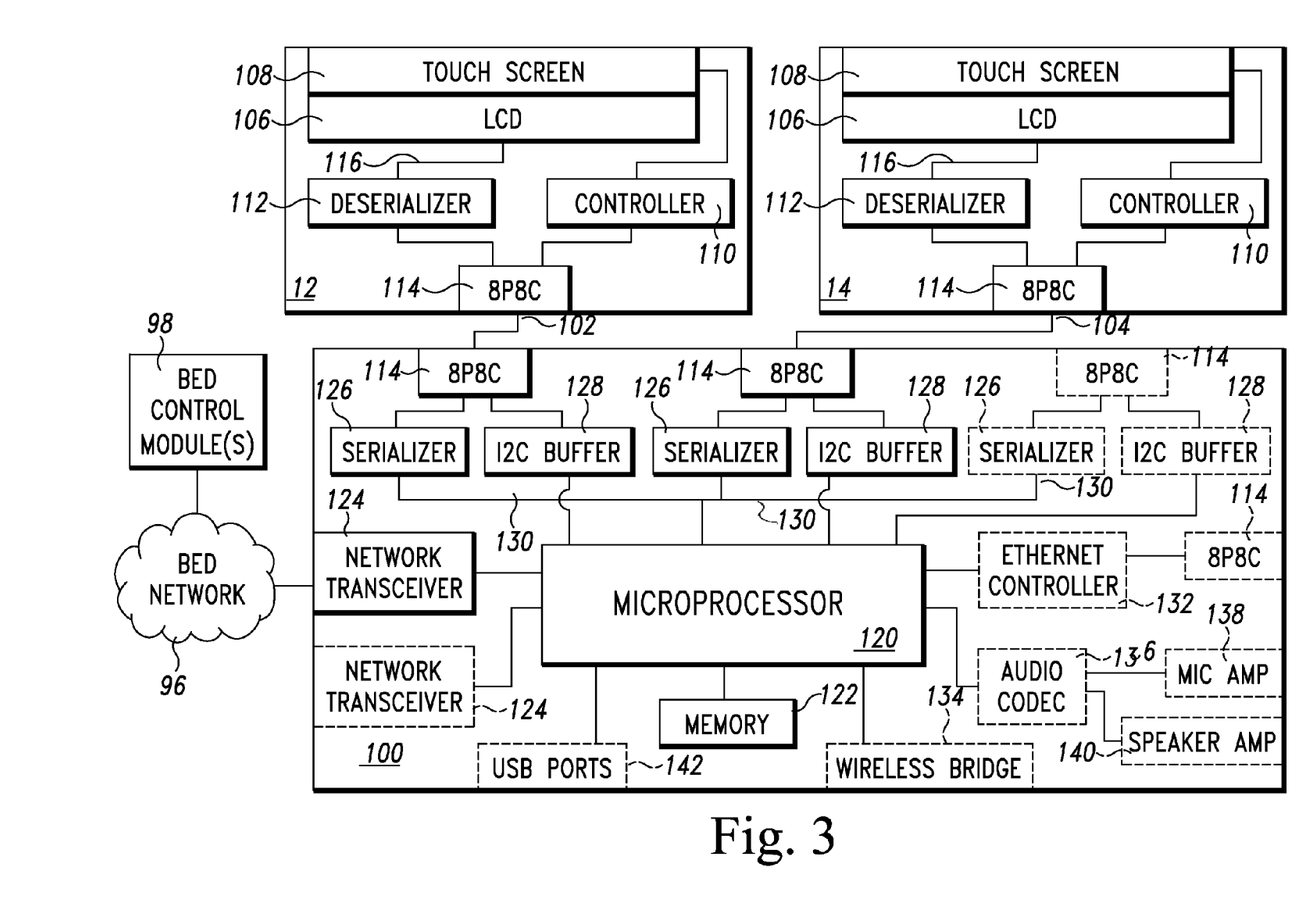
FIG. 3 is a simplified block diagram showing an electrical system of the person-support apparatus of FIG. 1, the electrical system including an interface module and a plurality of user interfaces.

Further details regarding the electrical components of the interface module 100 and of the user interfaces 12, 14, according to one illustrative embodiment of the electrical control system of the bed 10, are shown in FIG. 3. The user interface 12 is operably coupled to the interface module 100 via a dedicated data link 102, while the user interface 14 is operably coupled to the interface module 100 via a dedicated data link 104. The interface module 100 is generally configured to generate a plurality of synchronous graphics signals and transmit these synchronous graphics signals to user interfaces 12, 14 via the dedicated data links 102, 104. According to the present disclosure, the term "synchronous" refers to contemporaneous signals, transmissions, or operations which occur during the same, or substantially the same, time period and which typically include identical, or similar, signal content. The interface module 100 is also generally configured to receive command signals from one or more input devices of the user interfaces 12, 14 via the dedicated data links 102, 104, process the command signals, and transmit network messages to one or more bed control module 98 via the network 96. Thus, the interface module 100 interacts with the user interfaces 12, 14 to provide control of the operational and therapeutic functions or features of the bed 10. Once again, although only two user interfaces 12, 14 and two dedicated data links 102, 104 are shown in FIG. 3, it is contemplated that the interface module 100 may interact with any number of user interfaces.

In the illustrative embodiment, each of the user interfaces 12, 14 has the same construction. In other embodiments, the user interfaces of bed 10 may have distinct constructions from one another and include different components. Each user interface 12, 14 shown in FIG. 3 includes a liquid crystal display (LCD) 106, a touchscreen 108, a touchscreen controller 110, a deserializer 112, a connector 114, a power supply (not shown), and several interconnects (including parallel signal path 116). It should be appreciated that each illustrative user interface 12, 14 need not include any additional electrical components beyond the foregoing components. Such a construction may allow a user interface to have a relatively low profile and weight. In particular, each of the user interfaces 12, 14 lacks a transceiver, or other such circuitry, for coupling to the network 96 or communicating directly with the bed control module(s) 98 over the network 96. Rather, all interactions between the user interfaces 12, 14 and the bed control module(s) 98 take place via the interface module 100.

The LCD 106 functions as a graphical display for each user interface 12, 14, visually outputting text and graphics to a user of the bed 10, as described above with reference to FIG. 2. Each user interface 12, 14 may also include an input device, illustratively embodied in FIG. 3 as the touchscreen 108 and the controller 110. Similar to the touchscreen display 62 of user interface 60 (shown in FIG. 2), each touchscreen 108 may be positioned in proximity to the corresponding LCD 106 to form a touchscreen display that is configured to function both as an input device and an output device for each user interface 12, 14. In the illustrative embodiment, the touchscreen 108 includes a set of transparent, resistive layers and the controller 110 is embodied as a TSC2007 (available from Texas Instruments Incorporated of Dallas, Tex.) that is configured to measure the resistive network formed when the touchscreen 108 is touched by a user. In other embodiments, the touchscreen 108 may operate using any other known technology (e.g., capacitance) or may be supplemented or replaced with one or more other input devices (e.g., hardpanel controls 62). In any case, the controller 110 will generate a command signal in response to a user input and transmit the command signal to the interface module 100. By way of illustrative example, a command signal generated and transmitted by the TSC2007 controller 110 may include a "data available" interrupt and data formatted according to the I²C transmission protocol (which utilizes a serial data line and a serial clock line).

In the embodiment shown in FIG. 3, each user interface 12, 14 further includes a deserializer 112. As will be described in more detail below, each of the plurality of synchronous graphics signals generated by the interface module 100 and transmitted via one of the dedicated data links 102, 104 may illustratively be a serial graphics signal. In such embodiments, each serial graphics signal must be (re)converted into parallel graphics data for presentation to the LCD 106. In the illustrative embodiment, the deserializer 112 of the user interface 12 receives a serial data stream from the dedicated data link 102, decodes the serial data stream into graphics data, and provides the graphics data to the LCD 106 using the parallel signal path 116. The deserializer 112 of the user interface 14 performs these same operations synchronously with the deserializer 112 of the user interface 12. Each deserializer 112 may be illustratively embodied as a FIN24C μSerDes™ (available from Fairchild Semiconductor Corporation of South Portland, Me.) that is configured to operate as a deserializer. The parallel signal path 116 may be embodied as a flat, flexible connector (FFC) having 40 conductive signal paths, by way of illustrative example.

Signal paths communicatively couple both the controller 110 and the deserializer 112 to a connector 114 in each user interface 12, 14. Each connector 114 is positioned at or near an exterior surface of one of the user interfaces 12, 14 to allow coupling with one of the dedicated data links 102, 104. In some embodiments, each end of the dedicated data links 102, 104 may terminate in a plug, and the connector 114 may be embodied as a connecter socket 114 sized to receive one of the plugs. As shown in FIG. 3, each connector 114 is illustratively embodied as an 8-Position/8-Conductor, or "8P8C," modular connector (also referred to in the art as an RJ-45 connector). The dedicated data links 102, 104 shown in FIG. 3 are each illustratively embodied as a twisted pair serial cable having eight conductors (i.e., four twisted pairs). For instance, each dedicated data link 102, 104 may be a Category 5 cable, a Category 5e cable, a Category 6 cable, or the like. Both the 8P8C modular connectors 114 and the twisted pair serial cables 102, 104 may be wired according to the TIA/EIA-568-B standard, in some embodiments. It will be appreciated by those of skill in the art that other connector types and wiring standards are possible.

In the illustrative embodiment of the electrical control system of the bed 10 shown in FIG. 3, the interface module 100 includes a processor 120, a memory 122, at least one network transceiver 124, a plurality of transmitters 126, a plurality of I²C bus buffers 128, a plurality of connectors 114, a power supply (not shown), and several interconnects (including parallel signal path 130). In some embodiments, several of the foregoing components may be incorporated on a printed circuit board (PCB), while other components may be communicatively coupled to the PCB via, for example, a peripheral port. It will be appreciated that, in some embodiments, the interface module 100 may include additional components, sub-components, and other devices commonly found in a computing device (such as those shown in phantom in FIG. 3, and discussed below, and others not illustrated). By way of example, an additional transmitter 126, an additional I²C bus buffer 128, and an additional 8P8C modular connector 114 are shown in phantom in FIG. 3 to indicate that the interface module 100 may interact with any number of user interfaces on the bed 10. For each additional transmitter 126, buffer 128, and connector 114 present, the interface module 100 may support another user interface coupled to the interface module via another dedicated data link.

The interface module 100 includes a processor 120, which may be any type of processor capable of executing software/firmware, such as a microprocessor, digital signal processor, microcontroller, or the like. The processor 120 is illustratively embodied as an i.MX35 Multimedia Applications Processor (available from Freescale Semiconductor, Incorporated of Austin, Tex.) having a single processor core. In other embodiments, however, the processor 120 may be embodied as a multi-core processor and/or the interface module 100 may include one or more additional processors 120, each having one or more processor cores. The processor 120 is generally responsible for executing a software stack, which may include various applications, programs, libraries, and drivers resident on the interface module 100. The processor 120 is communicably coupled to each of the components of the interface module 100 (indirectly to the connectors 114 and the optional amplifiers 138, 140) by a number of interconnects, or signal paths.

The interface module 100 also includes a memory 122 that may be embodied as one or more memory devices or data storage locations including, for example, dynamic random access memory devices (DRAM), synchronous dynamic random access memory devices (SDRAM), double-data rate synchronous dynamic random access memory devices (DDR SDRAM), flash memory devices, and/or other memory devices. Although illustrated as a single memory device 122 in FIG. 3, it is contemplated that the interface module 100 may include multiple memory devices 122. In the illustrative embodiment, for instance, the memory 122 is embodied as one MT29F4G08AAC-WC NAND Flash device and four MT47H32M16 DDR SDRAM devices (each available from Micron Technology, Incorporated of Boise, Id.). Graphics data, including the informational and selectable display elements that provide the multi-level, menu-driven user interface for the bed 10, may be stored in the memory 122, and portions of the graphics data may be retrieved from the memory 122 by the processor 120 during operation. Furthermore, the applications, programs, libraries, and drivers that make up the software stack executed by the processor 120 may reside in memory 122.

At least one network transceiver 124 is included in the interface module 100 to facilitate communications between the processor 120 and one or more bed control modules 98 over the communications network 96 of the bed 10. As described herein, the interface module 100 is generally configured to receive command signals from the user interfaces 12, 14 via the dedicated data links 102, 104. When the interface module 100 receives a command signal, the processor 120 will evaluate the command signal to determine what input has been selected by a user. In some cases, the command signal may indicate the selection of an operational or therapeutic function or feature of the bed 10. In such cases, the processor 120 will then instruct the transceiver 124 to generate a network message on the communications network 96 that will result in one or more bed control modules 98 performing the selected operational or therapeutic function or feature. In one illustrative embodiment, the interface module 100 includes at least one TJA1051T High-Speed CAN Transceiver 124 (available from NXP Semiconductors of Eindhoven, The Netherlands) that is configured to send and receive network messages over a controller area network 96. In some embodiments, the interface module 100 may also include one or more additional network transceivers 124. The additional network transceiver(s) 124 may be used by the processor 120 to communicate with additional bed network(s) (possibly using a different network protocol than the network 96), where present.

As shown in FIG. 3, the interface module 100 further includes a plurality of serial interfaces for communicating with a plurality of user interfaces 12, 14. Each serial interface of the interface module 100 includes a transmitter 126, an $I^2C$ bus buffer 128, and a connector 114 communicatively coupled, via signal paths, to both the transmitter 126 and the $I^2C$ bus buffer 128. Each connector 114 is illustratively embodied in FIG. 3 as an 8P8C modular connector socket 114 sized to receive a plug at the terminal of one of the dedicated data links 102, 104. The $I^2C$ bus buffer 128 of each serial interface contains two bidirectional, open-drain buffer circuits (one for the serial data line and one for the serial clock line of the $I^2C$ bus). The buffers 128 are configured to isolate the $I^2C$ bus capacitance (<400 pF) in each dedicated data link 102, 104. Each $I^2C$ bus buffer 128 may be illustratively embodied as PCA9515A (available from Texas Instruments Incorporated of Dallas, Tex.).

The interface module 100 also includes a plurality of transmitters 126 which are configured to receive graphics data from the processor 120, generate a plurality of synchronous graphics signals, and transmit these synchronous graphics signals to the user interfaces 12, 14 via the dedicated data links 102, 104. Each of the transmitters 126 is communicatively coupled to the processor 120 via a parallel signal path 130, illustratively embodied as a parallel bus 130. During operation, the processor 120 retrieves graphics data from the memory 122 and outputs graphics data on the parallel bus 130. The graphics data output by the processor 120 is thereby synchronously provided to each transmitter 126 coupled to the parallel bus 130. Each transmitter 126 then generates a synchronous graphics signal based upon the graphics data and transmits this signal via the dedicated data link 102, 104 coupled to the corresponding connector 114. It will be appreciated that this operation results in the plurality of synchronous graphics signals reaching the user interfaces 12, 14 at substantially the same time (except for any transmission delays due to differing lengths of the dedicated data links 102, 104) and the graphics data being synchronously displayed on the LCDs 106 of both user interfaces 12, 14.

In the illustrative embodiment shown in FIG. 3, each of the plurality of transmitters 126 is embodied as a FIN24C µSerDes™ (available from Fairchild Semiconductor Corporation of South Portland, Me.) which is configured to operate as a serializer. Each serializer 126 receives graphics data via the parallel bus 130, converts this graphics data into a serial graphics signal, and transmits the serial graphics signal via the dedicated data link 102, 104 coupled to the corresponding connector 114. The serial graphics signal may be illustratively embodied as a differential serial data signal and a differential serial clock signal (using a total of four lines of one of the dedicated serial links). As mentioned above, where the plurality of transmitters 126 are embodied as serializers 126, the plurality of user interfaces 12, 14 will each include a deserializer 112 for reconverting the serial graphics signal into the graphics data.

The interface module 100 may optionally include additional electrical components, some of which are shown in FIG. 3, such as an Ethernet controller 132, a wireless bridge 134, an audio CODEC 136, a microphone amplifier 138, a speaker amplifier 140, and one or more universal serial bus (USB) ports 142, among other possible components. Via the Ethernet controller 132 and/or the wireless bridge 134, the interface module 100 may communicate with the one or more systems external to the bed 10. For instance, the interface module 100 may broadcast graphics data, or other bed status information, to a user interface external to the bed 10. The Ethernet controller 132 and/or the wireless bridge 134 may communicate with each of these systems via other hardware included in an external network, such as servers, routers, hubs, wireless access points, transceivers, and any other hardware provided by a healthcare environment in its facility communications network(s) (e.g., LAN, WAN, and/or Ethernet). Ethernet controller 132 may be illustratively embodied as an ENC28J60 Ethernet Controller and wireless bridge 134 may be illustratively embodied as a ZG2101MC WiFi Module (each available from Microchip Technology, Incorporated of Chandler, Ariz.).

The interface module 100 may also interact with or control one or more audio systems of the bed 10 using the audio CODEC 136, the microphone amplifier 138, and the speaker amplifier 140. For instance, one or more of the user interfaces 12, 14 may contain a microphone connected to the microphone amplifier 138 and/or one or more speakers connected to the speaker amplifier 140. The audio CODEC (digital coder-decoder) 136 may be configured to receive and process audio signals from the microphone amplifier 138 and to generate and transmit audio signals to the speaker amplifier 140. The audio CODEC 136 may communicate, via the processor 120, with one or more of systems external to the interface module 100 or the bed 10 (e.g., a nurse call system), as described above. Audio CODEC 136 may be illustratively embodied as a MAX9853 Stereo Audio CODEC and speaker amplifier 140 may be illustratively embodied as a MAX9715 Stereo Audio Amplifier (each available from Maxim Integrated Products, Incorporated of Sunnyvale, Calif.). The interface module 100 may also include one or more USB ports 142 (e.g., a host port, a device port, an On-The-Go port, or the like) to provide an updating/debugging interface for the module. In the illustrative embodiment of FIG. 3, the USB controllers for the port(s) 142 are incorporated within the i.MX35 processor 120.

Figure 4:
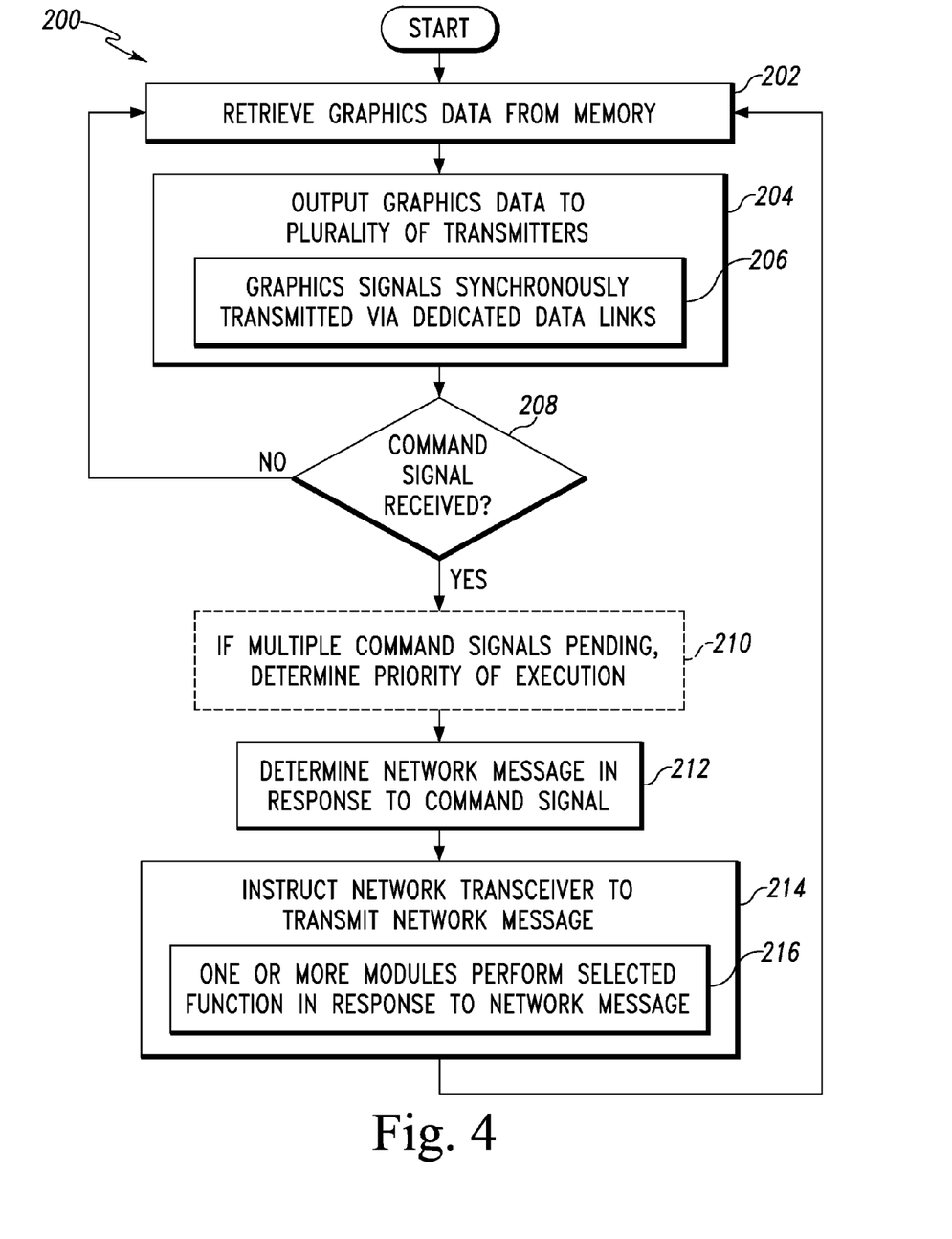
FIG. 4 is a simplified flowchart illustrating the operation of the interface module of FIG. 3.

Referring now to FIG. 4, an illustrative embodiment of a method of operating the interface module 100 of FIG. 3 is illustrated as a simplified flow diagram. Generally, the interface module 100 operates according to the algorithm 200 illustrated in FIG. 4 to synchronously provide graphics data to the plurality of user interfaces 12, 14, receive command signals from the plurality of user interfaces 12, 14, and communicate with one or more bed control modules 98 over the communications network 96 to provide control of the operational and therapeutic functions or features of the bed 10. The algorithm 200 may be performed, by way of example, by the processor 120 of the interface module 100 when executing one or more executable files stored in the memory 122. The memory 122 may include a plurality of instructions that, in response to being executed, result in the processor 120 performing some or all of the steps 202-216 illustrated in FIG. 4.

The algorithm 200 begins with step 202 in which the processor 120 retrieves portions of the graphics data stored in memory 122. The graphics data retrieved in step 202 corresponds to the informational and selectable display elements to be initially displayed on the LCDs 106 of the user interfaces 12, 14 of the bed 10. After step 202, the algorithm 200 proceeds to step 204 in which the processor 120 outputs the graphics data to the plurality of transmitters 126 via the parallel bus 130. As described above, this operation results in step 206 of the algorithm 200 in which the plurality of transmitters 126 generate a plurality of synchronous graphics signals and transmit these synchronous graphics signals to the user interfaces 12, 14 via the dedicated data links 102, 104. This, in turn, results in the graphics data being synchronously displayed on the LCDs 106 of both user interfaces 12, 14.

After step 204 (and step 206), the algorithm 200 proceeds to step 208 in which the processor 120 determines whether a command signal has been received from any of the user interfaces 12, 14. If the processor 120 determines that no command signals have been received, the algorithm 200 returns to the step 202 in which the processor 120 retrieves portions of the graphics data stored in memory 122. The graphics data retrieved during each iteration of step 202 may be the same graphics data as the previous iteration (where the status of the bed 10 remains unchanged) or may be new graphics data (to indicate a change in the status of the bed 10). If the processor 120 instead determines, during step 208, that a command signal has been received, the algorithm 200 proceeds to either step 210 (optional) or step 212. In some embodiments, steps 202-06 may be illustratively embodied as looping logic and step 208 may be illustratively embodied as an interrupt of the looping logic.

When a command signal has been received by the processor 120, the algorithm 200 proceeds to either step 210 (optional) or step 212. Optional step 210 is implemented when the processor 120 simultaneously receives more than one command signal or when a command signal is received by the processor 120 while other command signals are still pending execution. In optional step 210, the processor 120 determines a priority of execution for each of the pending command signals. For instance, when the processor 120 receives conflicting command signals from the user interfaces 12, 14, the processor 120 will implement priority logic to determine which, if any, of the command signals should be executed first.

After step 210 (or after step 208, where optional step 210 is not needed), the algorithm 200 proceeds to step 212 in which the processor 120 evaluates the received command signal to determine what input has been selected by a user. As described above, the command signal may indicate the selection of an operational or therapeutic function or feature of the bed 10. In step 212, the processor 120 will determine an appropriate network message which, when broadcast on the network 96, will cause one or more bed control modules 98 to perform the selected function or feature.

After step 212, the algorithm proceeds to step 214 in which the processor 120 instructs the network transceiver 124 to transmit the appropriate network message (determined in step 212) to the bed control modules 98 on the network 96. As described above, this operation results in step 216 of the algorithm 200 in which the one or more bed control modules 98 perform the selected operational or therapeutic function or feature (e.g., repositioning the various sections of the articulated mattress support deck 36). After step 214 (and step 216), the algorithm 200 returns to the step 202 in which the processor 120 retrieves portions of the graphics data stored in memory 122. The graphics data retrieved during this iteration of step 202 will typically be new, or updated, graphics data (to indicate a change in the status of the bed 10, due to the performance of the selected function or feature). For instance, the updated graphics data may include information regarding the status of bed 10, a description of the selected function or feature, and/or a menu of control options for the selected function or feature. It will be appreciated that the algorithm 200 will generally run in a continuous loop, as just described, so long as the bed 10 is connected to a power source.

Although certain illustrative embodiments have been described in detail above, variations and modifications exist within the scope and spirit of this disclosure as described and as defined in the following claims.

The invention claimed is:
1. A person-support apparatus comprising
a communications network coupling a plurality of modules, each of the plurality of modules configured to control a function of the person-support apparatus,
a first user interface including a first input device and a first graphical display device,
a second user interface including a second input device and a second graphical display device, and
an interface module coupled to the communications network, the interface module configured to transmit a first synchronous graphics signal to the first user interface via a first dedicated serial link and transmit a second syn- chronous graphics signal to the second user interface via a second dedicated serial link,
wherein the first user interface further comprises a first deserializer configured to convert the first synchronous graphics signal into a graphic and the second user interface further comprises a second deserializer configured to convert the second synchronous graphics signal into the graphic, whereby the graphic is displayed on both the first and second graphical display devices.

2. The person-support apparatus of claim 1, wherein the interface module comprises a first serializer configured to convert the graphic into the first synchronous graphics signal and a second serializer configured to convert the graphic into the second synchronous graphics signal.

3. The person-support apparatus of claim 1, wherein the interface module is configured to receive a command signal from either the first input device via the first dedicated serial link or the second input device via the second dedicated serial link and generate a network message on the communications network in response to the command signal.

4. The person-support apparatus of claim 3, further comprising an articulated support surface, one of the plurality of modules being operable to reposition the articulated support surface in response to the network message.

5. The person-support apparatus of claim 1, wherein the first user interface is remote from the interface module.

6. The person-support apparatus of claim 5, wherein the second user interface is both remote from the interface module and remote from the first user interface.

7. An interface module comprising a processor, a transceiver configured to communicate with a plurality of bed control modules over a communications network, a plurality of serial interfaces, each serial interface configured to communicate with a touchscreen display device over a dedicated serial link, and a memory including a plurality of instructions which, when executed by the processor, cause the processor to (i) retrieve graphics data from the memory and (ii) output the graphics data to the plurality of serial interfaces to be synchronously transmitted to the touchscreen display devices; wherein the memory further comprises instructions which, when executed by the processor, cause the processor to (i) receive a first command signal via one of the plurality of serial interfaces, (ii) determine a network message in response to the first command signal, and (iii) instruct the transceiver to transmit the network message.

8. The interface module of claim 7, wherein the memory further comprises instructions which, when executed by the processor, cause the processor to (i) receive a second command signal via another of the plurality of serial interfaces and (ii) determine a priority of execution for the first and second command signals.

9. The interface module of claim 7, wherein the first command signal indicates a therapy selected by a user and the network message will cause one or more of the plurality of bed control modules to deliver the selected therapy.

10. The interface module of claim 9, wherein the memory further comprises instructions which, when executed by the processor, cause the processor to (i) retrieve updated graphics data from the memory in response to the first command signal and (ii) output the updated graphics data to the plurality of serial interfaces to be synchronously transmitted to the touchscreen display devices.

11. The interface module of claim 10, wherein the updated graphics data includes at least one of a bed status, a description of the selected therapy, and a menu of control options for the selected therapy.

12. An apparatus for controlling a plurality of modules coupled to a communications network of a bed, the apparatus comprising
an interface module including a transceiver coupled to the communications network, a processor configured to output graphics data, and a plurality of transmitters configured to receive the graphics data and generate a plurality of synchronous graphics signals,
a plurality of user interfaces, each user interface including a graphical display device, and
a plurality of dedicated data links, each dedicated data link coupled to one of the plurality of transmitters and coupled to one of the plurality of user interfaces;
wherein each of the plurality of user interfaces further comprises a deserializer configured to receive a serial graphics signal via the dedicated data link coupled to the user interface, convert the serial graphics signal into the graphics data, and provide the graphics data to the graphical display device of the user interface via a parallel signal path.

13. The apparatus of claim 12, wherein each of the plurality of user interfaces does not include a transceiver coupled to the communications network.

14. The apparatus of claim 12, wherein each of the plurality of transmitters comprises a serializer configured to receive the graphics data from the processor via a parallel signal path, convert the graphics data into a serial graphics signal, and transmit the serial graphics signal via the dedicated data link coupled to the transmitter.

15. The apparatus of claim 12, wherein each of the plurality of dedicated data links comprises a twisted pair serial cable.

16. The apparatus of claim 12, wherein each of the plurality of graphical displays is configured to output the graphics data to provide a multi-level, menu-driven user interface for the bed.

17. The apparatus of claim 16, wherein the graphics data includes at least one of a bed status, a menu of selectable bed therapies, a description of a selected therapy, a menu of control options for the selected therapy, and a record of patient information.

18. The apparatus of claim 12, wherein each of the plurality of user interfaces further comprises an input device configured to generate a command signal in response to a user interaction and transmit the command signal to the interface module via the dedicated data link coupled to the user interface.

19. The apparatus of claim 18, wherein the input device of each user interface comprises a touchscreen positioned in proximity to the graphical display device of the user interface and a controller coupled to the touchscreen, the controller being configured to generate the command signal in response to a user interaction with the touchscreen.

20. The apparatus of claim 18, wherein the processor is configured to evaluate the command signal and instruct the transceiver to generate a network message on the communications network in response to the command signal.

21. The apparatus of claim 12, wherein at least one of the plurality of user interfaces is remote from the interface module.

* * * * *